(12) United States Patent
Brummel et al.

(10) Patent No.: US 9,909,938 B2
(45) Date of Patent: Mar. 6, 2018

(54) SENSOR ARRANGEMENT AND METHOD FOR DETERMINING THE MECHANICAL SURFACE STRESSES AND/OR THE MICROSTRUCTURE STATE

(71) Applicant: SIEMENS AKTIENGESELLSCHAFT, München (DE)

(72) Inventors: Hans-Gerd Brummel, Berlin (DE); Uwe Pfeifer, Berlin (DE)

(73) Assignee: SIEMENS AKTIENGESELLSCHAFT (DE)

( * ) Notice: Subject to any disclaimer, the term of this patent is extended or adjusted under 35 U.S.C. 154(b) by 0 days.

(21) Appl. No.: 14/911,120

(22) PCT Filed: Aug. 25, 2014

(86) PCT No.: PCT/EP2014/067964
§ 371 (c)(1),
(2) Date: Feb. 9, 2016

(87) PCT Pub. No.: WO2015/032638
PCT Pub. Date: Mar. 12, 2015

(65) Prior Publication Data
US 2016/0195438 A1    Jul. 7, 2016

(30) Foreign Application Priority Data
Sep. 3, 2013    (EP) .................................... 13182806

(51) Int. Cl.
*G01R 33/18*    (2006.01)
*G01L 1/12*    (2006.01)
(Continued)

(52) U.S. Cl.
CPC ............ *G01L 1/125* (2013.01); *G01M 5/0041* (2013.01); *G01N 27/902* (2013.01); *G01N 27/904* (2013.01)

(58) Field of Classification Search
CPC . G01L 1/125; G01L 3/102; G01L 1/12; G01L 1/127; G01L 3/104; G01L 5/10;
(Continued)

(56) References Cited

U.S. PATENT DOCUMENTS

| 3,535,625 A | 10/1970 | Pratt |
| 5,297,439 A * | 3/1994 | Tyren .................... G01L 3/102 324/209 |

(Continued)

FOREIGN PATENT DOCUMENTS

| EP | 2 574 912 A1 | 4/2013 |
| GB | 2 456 583 A | 7/2009 |
| JP | S57 44850 A | 3/1982 |

OTHER PUBLICATIONS

International Search Report for PCT Application No. PCT/EP2014/067964, dated Nov. 12, 2014.

*Primary Examiner* — Vinh Nguyen
(74) *Attorney, Agent, or Firm* — Schmeiser Olsen & Watts LLP (57) ABSTRACT

A sensor assembly for detecting surfaces stresses and/or the microstructure state of a ferromagnetic workpiece, wherein at least one first base coil system having a first directional sensitivity is provided, at least one second base coil system having a second directional sensitivity is provided, and at least one third base coil system having a third direction and a third directional sensitivity is provided, and wherein at least the first base coil system and the second base coil system form a first differential angle and the second base coil system and the third base coil system form a second differential angle, and wherein the first base coil system, the
(Continued)

second base coil system, and the third base coil system are arranged such that the mechanical surface stresses of the workpiece can be at least partially determined. A method for determining the mechanical surface stresses is also provided.

20 Claims, 3 Drawing Sheets

(51) Int. Cl.
*G01N 27/90* (2006.01)
*G01M 5/00* (2006.01)

(58) Field of Classification Search
CPC ......... G01L 1/255; G01L 3/103; G01L 3/105; G01L 5/0023; G01R 15/148; G01R 33/0286; G01R 33/02; G01R 33/0206; G01R 33/028; G01R 33/07; G01R 33/09; G01R 33/18; G01R 27/02; G01R 33/34084; G01B 7/16
See application file for complete search history.

(56) References Cited

U.S. PATENT DOCUMENTS

| | | | | |
|---|---|---|---|---|
| 5,351,555 A | * | 10/1994 | Garshelis | G01L 3/102 336/30 |
| 2002/0153882 A1 | * | 10/2002 | Grimes | G01N 27/72 324/209 |
| 2012/0126833 A1 | | 5/2012 | Dooley | |

* cited by examiner

SENSOR ARRANGEMENT AND METHOD FOR DETERMINING THE MECHANICAL SURFACE STRESSES AND/OR THE MICROSTRUCTURE STATE

CROSS-REFERENCE TO RELATED APPLICATIONS

This application claims priority to PCT Application No. PCT/EP2014/067964, having a filing date of Aug. 24, 2014, based off of European application No. EP 13182806.3 having a filing date of Sep. 3, 2013, the entire contents of which are hereby incorporated by reference.

FIELD OF TECHNOLOGY

The following relates to a sensor arrangement for detecting surface stresses and/or the microstructure state of a ferromagnetic workpiece and to a method for determining the mechanical surface stresses and/or the microstructure state.

BACKGROUND

The determination of the surface stress state and/or the microstructure state is an important task when monitoring the stress on mechanical workpieces. Various measuring methods exist for this purpose. One of the most frequently used methods operates with strain gauges which have to be applied to the surface at the measuring point for this purpose using a complicated method. In the case of moving workpieces, a telemetry system for active supply and transmission of measured values is additionally required. Furthermore, contactlessly operating optical methods are also known. However, both are very complicated.

SUMMARY

An aspect relates to a sensor arrangement which solves the above-mentioned problem. Another object is to specify a method for determining the mechanical surface stresses and/or the microstructure state of a ferromagnetic workpiece.

A further aspect is achieved with the specification of a sensor arrangement for detecting surface stresses and/or the microstructure state of a ferromagnetic workpiece:

at least one first basic coil system having a first direction and a first directional sensitivity being provided, at least one second basic coil system having a second direction and a second directional sensitivity being provided, at least one third basic coil system having a third direction and a third directional sensitivity being provided, at least the first basic coil system and the second basic coil system forming a first differential angle and the second basic coil system and the third basic coil system forming a second differential angle, and the first basic coil system being arranged outside the second directional sensitivity and the third directional sensitivity, the second basic coil system being arranged outside the first directional sensitivity and the third directional sensitivity and the third basic coil system being arranged outside the first directional sensitivity and the second directional sensitivity, with the result that the mechanical surface stresses of the workpiece can be at least partially determined.

The proposed embodiment of the invention is based on the use of a specially configured and arranged sensor arrangement comprising a plurality of basic coil systems. A downstream computing algorithm determines the magnitude and the direction of the acting mechanical surface stresses. In order to determine the permeability and therefore the mechanical state of stress in a direction-dependent manner, it is also necessary to magnetically permeate the workpiece surface in a manner which is as direction-sensitive as possible. In this case, the mechanical stresses are detected contactlessly, that is to say the sensor arrangement does not come into direct contact with the surface. No auxiliary means have to be applied to the surface either and there is no need to machine the workpiece surface provided that there is a particular roughness or evenness with respect to the sensor arrangement. The sensor arrangement is able to determine the main state of stress at the measuring point. The vector components of the tensile stresses or compressive stresses and the shear stresses in any desired orientation directions can then be calculated from the main state of stress.

The sensor arrangement can also be advantageously used on moving workpieces, that is to say on rotating shafts, for example. Embodiments of the invention allow a contactless and application-free measuring principle which can be used to measure a very large number of measuring points on a workpiece within a short time or can even be used to carry out surface mapping. It goes without saying that the sensor arrangement may also comprise yet further basic coil systems. Using more than three such basic coil systems makes it possible to produce additional redundancies or to also carry out plausibility checks, for example.

A basic coil system preferably comprises at least one excitation coil and a receiver coil. This is a very simple embodiment of a basic coil system.

In a preferred configuration, the excitation coil and the receiver coil have a coil core with a coil core diameter. The directional sensitivity is now given by the ratio of the distance between the two coil cores and/or by the ratio of the two coil core diameters.

The directional sensitivity of the arrangement results from the ratio of the diameter and the distance between the coil cores. Small core diameters and large core distances result in a very direction-sensitive sensor arrangement. However, with large core distances, it must be borne in mind that an inhomogeneous stress distribution may exist in the area of influence and is then virtually integrated, that is to say averaged in terms of the area, by the coil system. Therefore, when dimensioning the coil system, it is advantageous to strive for a compromise between directional sensitivity and spatial resolution.

In a preferred configuration, the first basic coil system and/or the second basic coil system and/or the third basic coil system comprise(s) an excitation coil and a receiver coil which are arranged on a U ferrite core. The first basic coil system and/or the second basic coil system and/or the third basic coil system preferably comprise(s) an excitation coil and a first receiver coil and a second receiver coil which are arranged on a U ferrite core and/or EI ferrite core, the excitation coil being arranged between, in particular centrally between, the first receiver coil and the second receiver coil. It goes without saying that other arrangements may also be possible.

At least two excitation coils of the three basic coil systems preferably have a series circuit. In addition to the adjustment of the receiving coil systems, identical excitation should be ensured in this case, in particular. A sensitivity which is as identical as possible is now achieved by means of an electrical series circuit of the excitation coils, for example, during the electrical connection of the first basic coil system and the second basic coil system and the third basic coil system. Other electrical or electronic measures are also possible in order to achieve a sensitivity of the different basic coil systems which is as identical as possible.

In addition to the arrangement of separate basic coil systems with a different ferrite core, these basic coil systems may also be combined on one ferrite core, for example on a composite coil. However, for this purpose, it is necessary to shift the geometry of the arrangement to the shape of the ferrite core (or generally the coil core). This means that the functionality previously implemented in three basic coil systems, namely the magnetic permeation of a surface region in at least three different directions, is now implemented using only one coil former or ferrite core.

The at least three basic coil systems are preferably provided by a composite coil system which, as a first basic coil system, comprises a composite excitation coil and a first composite receiver coil, as a second basic coil system, comprises the composite excitation coil and a second composite receiver coil and, as a third basic coil system, comprises the composite excitation coil and a third composite receiver coil as well as a further, fourth composite receiver coil, the composite excitation coil and the four composite receiver coils being arranged on a common ferrite core. Furthermore, the four receiver coils are preferably at the same distance from the composite excitation coil, adjacent receiver coils each being arranged at the same distance from one another. In addition to a symmetrical arrangement, this also has the advantage of simple systems of equations, which is favorable for calculating the surface stress. In addition, asymmetries in the production of the sensor arrangement are compensated for in this manner.

The at least three basic coil systems are preferably provided by a composite coil system which, as a first basic coil system, comprises a composite excitation coil and a first composite receiver coil, as a second basic coil system, comprises the composite excitation coil and a second composite receiver coil and, as a third basic coil system, comprises the composite excitation coil and a third composite receiver coil, the three composite receiver coils and the composite excitation coil being arranged on a common ferrite core. In a preferred configuration, the three composite receiver coils are at the same distance from the composite excitation coil, adjacent receiver coils each being arranged at the same distance from one another. In a preferred configuration, the at least three basic coil systems are provided by a composite coil system which, as a first basic coil system, comprises a composite excitation coil and a first composite receiver coil, as a second basic coil system, comprises the composite excitation coil and a second composite receiver coil and, as a third basic coil system, comprises the composite excitation coil and a third composite receiver coil, a fourth composite receiver coil, a fifth composite receiver coil and a sixth composite receiver coil, the six composite receiver coils and the composite excitation coil being arranged on a common ferrite core. The six composite receiver coils are preferably at the same distance from the composite excitation coil, adjacent receiver coils each being arranged at the same distance from one another. In addition to a symmetrical arrangement, this also has the advantage, as above, of simple systems of equations which are favorable for calculating the surface stress. In addition, asymmetries in the production of the sensor arrangement are compensated for in this manner. In this case too, all composite coils are arranged on a common ferrite core.

In the case of a plurality of coils for each direction system, the receiving coils of these composite systems should preferably be operated in a series circuit.

The separate basic coil systems and/or the coil systems assigned to an orientation direction on the common ferrite core are arranged at particular differential angle orientations with respect to one another.

The first differential angle is preferably equal to the second differential angle and is, in particular, 45 degrees. Alternatively, the first differential angle and the second differential angle are 60 degrees. The first differential angle and the second differential angle may also be 120 degrees. In addition to a symmetrical arrangement, the advantage of simple systems of equations for subsequently determining the surface stress of the workpiece should also be mentioned here. In addition, particular asymmetries in the production of the sensor arrangement are also compensated for here in this manner. Any desired differential angles are likewise possible.

The coil axis is defined by virtue of the fact that it runs in the center of the coil in a perpendicular manner through a plane formed by the turns of the coil. In this case, the arrangement of the basic coil systems and/or the composite coil system with respect to the surface of the workpiece is selected in such a manner that an orthogonal orientation of the coil axes with respect to the workpiece surface is achieved, that is to say the open cross sections of the coil limbs are parallel to the workpiece surface. In this case, the sensor arrangement is at a nominal distance from this surface of the ferromagnetic workpiece, at least the first basic coil system and the second basic coil system and the third basic coil system being at a distance of at most 20% of this nominal distance from one another. However, if the sensor arrangement has robust distance compensation, this value may naturally also be higher. The sensor arrangement can also be positioned at a short distance from all points of the workpiece surface.

In a preferred configuration, at least the first basic coil system and the second basic coil system and the third basic coil system are arranged on a suitable holding device. This facilitates handling.

The second aspect based on the method is achieved by specifying a method for determining the mechanical surface stresses and/or the microstructure state of a ferromagnetic workpiece by means of the following steps:

determining three independent measured values by means of a sensor arrangement as claimed in one of the preceding claims, determining the direction-dependent permeability at a particular measuring point by means of a computing algorithm.

The method makes it possible to magnetically permeate the workpiece surface in a direction-sensitive manner in order to determine the permeability and therefore the mechanical state of stress in a direction-dependent manner. The subsequent determination of the mechanical state of stress is enabled by using the magnetoelastic effect. The mechanical stresses are detected contactlessly using this method, that is to say the sensor arrangement does not come into direct contact with the surface. No auxiliary means need to be applied to the surface either and there is no need to machine the workpiece surface. The proposed method therefore operates contactlessly and in an application-free manner, that is to say the measurement can be carried out at any desired surface points of the workpiece without apparatuses having to be fitted there. The contactless and application-free method therefore allows a very large number of measuring points on an object to be measured within a short time or even allows surface mapping to be carried out.

A plurality of measuring points of the workpiece are preferably determined and it is possible to determine a direction-dependent permeability therefrom, and the internal stress tensor is therefore mapped.

BRIEF DESCRIPTION

Some of the embodiments will be described in detail, with reference to the following figures, wherein like designations denote like members, wherein.

On mechanically stressed workpieces, a multi-axis state of stress which can be considered to be two-dimensional in an infinitesimally thin surface layer develops as a result of the acting forces and torques. The direction-dependent state of stress is determined with the aid of the magnetoelastic effect. This effect represents a relationship between mechanical properties (mechanical state of stress) and a magnetic material property, the permeability.

Embodiment of the proposed invention is based on the use of a specially configured and arranged sensor arrangement comprising a plurality of basic coil systems. A downstream computing algorithm determines the magnitude and the direction of the acting mechanical surface stresses. In order to determine the permeability and therefore the mechanical state of stress in a direction-dependent manner, it is also necessary to magnetically permeate the workpiece surface in a manner which is as direction-sensitive as possible.

DETAILED DESCRIPTION

Figure 1:
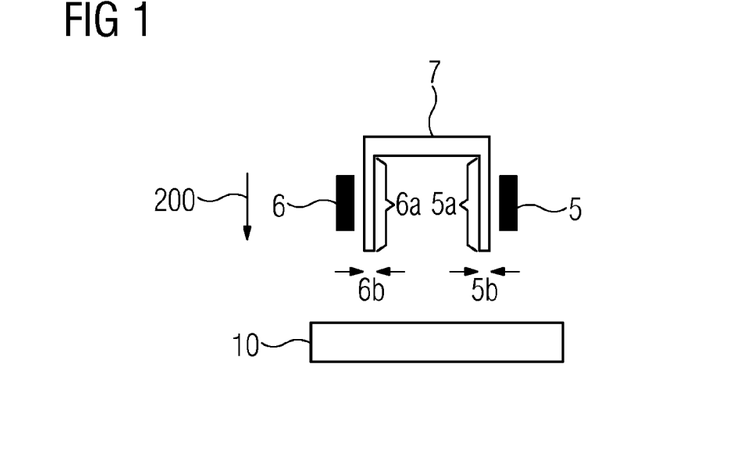
FIG. 1 schematically shows a first example of an individual basic coil system with an associated workpiece.

FIG. 1 shows a first example of a basic coil system. The latter comprises at least one excitation coil 6 and a receiver coil 5. In this case, the excitation coil 6 and the receiver coil 5 are arranged on a common U ferrite core 7. The receiver coil 5 comprises a coil core 5a with a coil core diameter 5b, and the excitation coil 6 likewise comprises a coil core 6a with a coil core diameter 6b. In this case, the coil core 5a and the coil core 6a may be arranged on the limbs of the U ferrite core. The directional sensitivity is predefined by the ratio of the distance between the coil core 6a and the coil core 5a and by the ratio of the coil core diameter 6b and the coil core diameter 5b.

Figure 2:
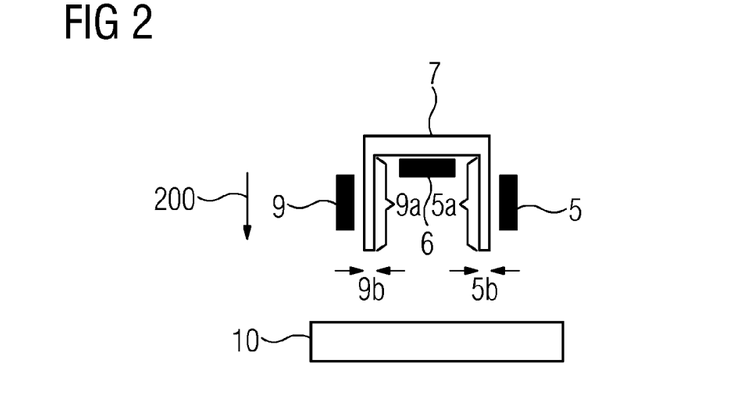
FIG. 2 schematically shows a second example of an individual basic coil system with an associated workpiece.

FIG. 2 shows a second example of a further basic coil system. The latter comprises an excitation coil 6, a first receiver coil 5 and a second receiver coil 9 which are arranged on a U ferrite core 7. The excitation coil 6 is arranged centrally between the first receiver coil 5 and the second receiver coil 9. In this case, the two receiver coils 5, 9 are arranged on the limbs of the U ferrite core 7.

Figure 3:
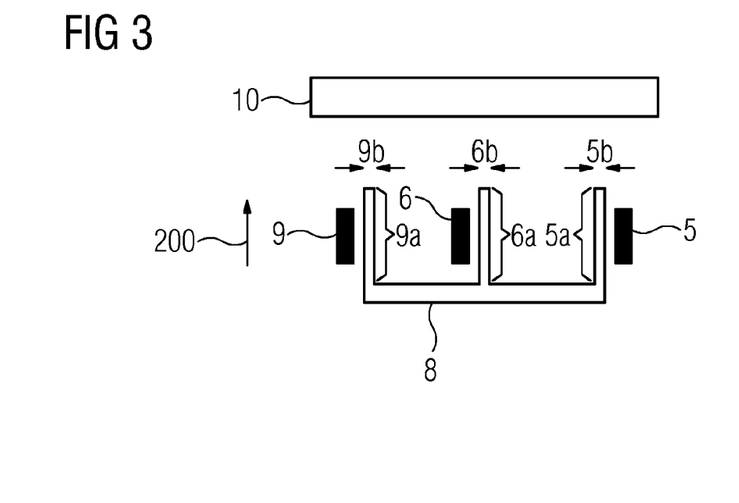
FIG. 3 schematically shows a third example of an individual basic coil system with an associated workpiece.

FIG. 3 shows a third example of a further basic coil system. The latter comprises an excitation coil 6, a first receiver coil 5 and a second receiver coil 9 which are arranged on an E ferrite core 8. In this case, the excitation coil 6 is arranged centrally between the first receiver coil 5 and the second receiver coil 9. In this case, the two receiver coils 5, 9 and the excitation coil 6 are arranged on the limbs of the E ferrite core 8.

It goes without saying that other ferrite cores, in particular EI ferrite cores or else C ferrite cores etc., can also be used. The basic coil systems illustrated are therefore only exemplary and are used for understanding.

Figure 4:
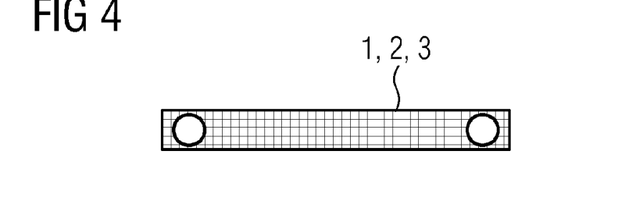
FIG. 4 schematically shows a schematic illustration (plan view) of the basic coil systems from FIG. 3, FIG. 2 and FIG. 1.

The basic coil system in FIG. 1, 2 or 3 is schematically illustrated in a unified manner as a hatched bar below, as shown in FIG. 4. In this case, the bar may be respectively numbered 1, 2 or 3, depending on whether the first basic coil system, the second basic coil system or the third basic coil system is involved. This means that one of the basic coil systems described above can be respectively used for a hatched bar in the subsequent figures. It goes without saying that other basic coil systems, for example on an EI ferrite core, which are not expressly described or cited, can also be used.

Figure 5:
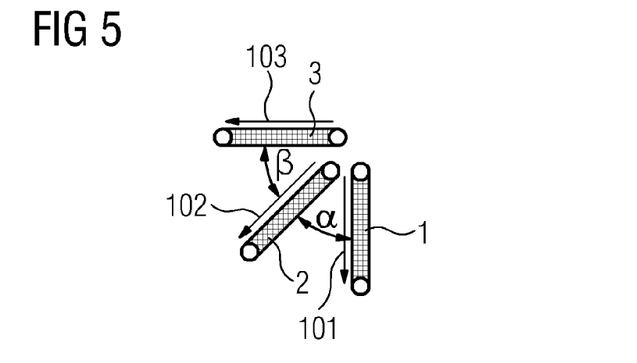
FIG. 5 schematically shows a first example of a sensor arrangement with a differential angle of 45°.

FIG. 5 shows, in a highly schematic manner, a first example of a first sensor arrangement according to embodiments of the invention for detecting surface stresses. The sensor arrangement consists of at least one first basic coil system 1 having a first direction 101 and a first directional sensitivity. In this case, one of the basic coil systems mentioned above can be used as the first basic coil system 1. It goes without saying that other basic coil systems with an EI ferrite core etc. can also be used.

The sensor arrangement also comprises at least one second basic coil system 2 having a second direction 102 and a second directional sensitivity. The sensor arrangement also comprises at least one third basic coil system 3 having a third direction 103 and a third directional sensitivity. The first basic coil system 1 and the second basic coil system 2 form a first differential angle α and the second basic coil system 2 and the third basic coil system 3 form a second differential angle β. In this case, the basic coil systems 1, 2, 3 each correspond to one of the basic coil systems from FIG. 1, 2 or 3.

In this case, the first direction 101 and the second direction 102 and the third direction 103 respectively form a differential angle α, β, where α, β are greater than 0 degrees. In addition, the directions 101, 102, 103 are arranged in such a manner that the first basic coil system 1 is arranged outside the second and third directional sensitivities, the second basic coil system 2 is arranged outside the first and third directional sensitivities and the third basic coil system 3 is arranged outside the first and second directional sensitivities.

In the example in FIG. 5, the first basic coil system 1 and the second basic coil system 2 also have a differential angle α and the second basic coil system 2 and the third basic coil system 3 have a differential angle β, the first differential angle α and the second differential angle β each being 45 degrees. In this case, the three basic coil systems 1, 2, 3 may be fitted to a holding arrangement (not shown).

Figure 6:
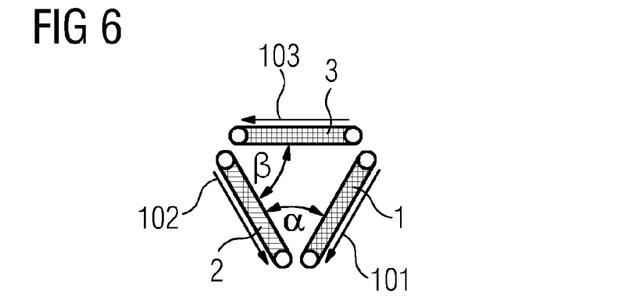
FIG. 6 schematically shows a second example of a sensor arrangement with a differential angle of 60°

FIG. 6 shows a second example of a second sensor arrangement according to embodiments of the invention having basic coil systems according to embodiments of the invention, in which the first basic coil system 1 and the second basic coil system 2 have a first differential angle α and the second basic coil system 2 and the third basic coil system 3 have a second differential angle β, the first differential angle α and the second differential angle β being 60 degrees. In this case, one of the basic coil systems mentioned above can be used as the respective basic coil system. It goes without saying that basic coil systems having an EI ferrite core etc. can also be used. In this case too, the directional sensitivities of a respective basic coil system are outside the other two directional sensitivities of the two other basic coil systems.

Figure 7:
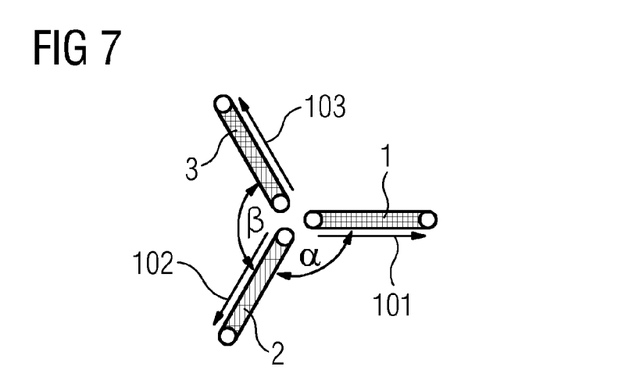
FIG. 7 schematically shows a third example of a sensor arrangement with a differential angle of 120°.

FIG. 7 shows a third example of a third sensor arrangement according to embodiments of the invention having basic coil systems according to embodiments of the invention, in which the first basic coil system 1 and the second basic coil system 2 have a first differential angle α and the second basic coil system 2 and the third basic coil system 3 have a second differential angle β, the first differential angle α and the second differential angle β being 120 degrees. In this case, one of the basic coil systems mentioned above can be used as the basic coil system 1, 2 or 3. It goes without saying that basic coil systems having an EI ferrite core etc. can also be used. In this case too, the directional sensitivities of a respective basic coil system are outside the other two directional sensitivities of the two other basic coil systems.

In addition to symmetry, the arrangement at the differential angle of 45 degrees, 60 degrees, 90 degrees (not shown) or 120 degrees, for example, also has the advantage of simple systems of equations which are favorable for determining the surface stress. In addition, asymmetries which lie in the production or handling of the sensor arrangement are possibly compensated for in this manner.

In this case, each of the basic coil systems described above can be used as the basic coil system and can naturally also be combined with one another. The basic coil systems which have not been mentioned and are arranged on a C core or an EI core, for example, can naturally also be used.

The directional sensitivity of the arrangement results from the ratio of the diameter and the distance between the coil cores 6a, 5a, 9a. Small core diameters and large core distances result in a very direction-sensitive sensor arrangement. However, with large core distances, it must be borne in mind that an inhomogeneous stress distribution exists in the area of influence and is then virtually integrated, that is to say averaged in terms of the area, by the coil system. Therefore, when dimensioning the coil system, it is necessary to strive for a compromise between directional sensitivity and spatial resolution.

When microstructures of the workpiece 10 (FIGS. 1, 2, 3) are changed, the permeability of the material, which can be substantially described with the aid of the internal stress tensor, likewise changes. If the permeability of the workpiece 10 is monitored, in particular monitored continuously, the change in the microstructure of the workpiece 10 can be inferred from the change in the directional permeability. The determination of a spatially resolved internal stress tensor with the aid of the magnetoelastic measuring principle now makes it possible to detect material properties and their changes. For this purpose, the complete internal stress tensor must be determined. The internal stress tensor contains, as information parameters, the amplitude of the main stresses and the position or angular orientation of the main stress system.

This can be achieved using the sensor arrangement according to embodiments of the invention. These three independent measured values can be used, in particular, to determine either the three stress components or the characteristic values of the main state of stress which can in turn be used to determine the internal stress tensor. The surface of the workpiece 10 is preferably scanned using the sensor arrangement. Since the permeability of the workpiece 10 changes as a function of the stress, it can be used to determine the stress and fatigue of a workpiece.

In this case, the mechanical stresses are detected in a contactless manner, that is to say the sensor arrangement does not come into direct contact with the surface of the workpiece 10. No auxiliary means need to be applied to the surface either and there is no need to machine the workpiece surface provided that there is a certain roughness or evenness with respect to the size of the sensor head. The sensor arrangement according to embodiments of the invention operates contactlessly and in an application-free manner, that is to say the measurement can be carried out at any desired surface points of the workpiece 10 without apparatuses having to be fitted there. The sensor arrangement according to embodiments of the invention can be positioned at a short distance from all points of the workpiece surface 10, in particular between 0.5 mm and 1 mm, provided that there is a certain evenness of the surface in relation to the diameter of the sensor arrangement. The maximum distance difference inside the basic coil systems 1, 2, 3 in relation to one another should be no more than 20% of the nominal distance in the direction of the surface 200 (FIGS. 1, 2, 3).

In order to test material properties in a non-destructive manner, the sensor arrangement can continuously scan the workpiece 10; surface mapping can even be carried out here.

In addition to the arrangement of separate basic coil systems, these basic coil systems can also be combined on a ferrite core. For this purpose, however, it is necessary to shift the geometry of the arrangement to the shape of the ferrite core (or generally the coil core), as shown below using some examples.

Figure 8:
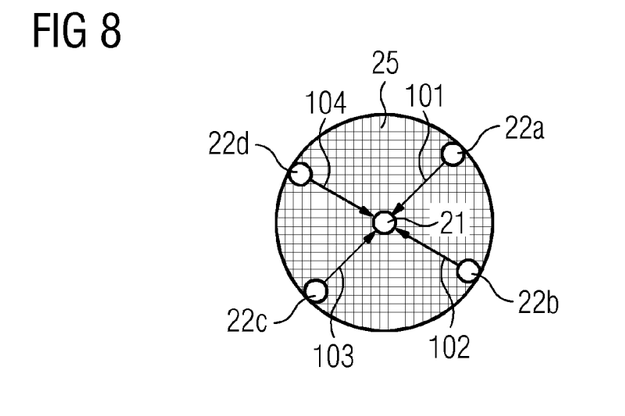
FIG. 8 schematically shows a first composite coil system as a fourth example of a sensor arrangement.

FIG. 8 shows such a first sensor arrangement which is provided by a composite coil system 20. The latter has, as a first basic coil system, a composite excitation coil 21 and a first composite receiver coil 22a having a first direction 101 and a first directional sensitivity, as a second basic coil system, has the composite excitation coil 21 and a second composite receiver coil 22b, a second direction 102 and a second directional sensitivity. A third basic coil system is the composite excitation coil 21 and a third composite receiver coil 22c, a third direction 103 and a third directional sensitivity. The composite excitation coil 21 and the fourth composite receiver coil 22d are a further basic coil system having a fourth direction 104 and a fourth directional sensitivity, the composite excitation coil 21 and the four composite receiver coils 22a, b, c, d being arranged on a common ferrite core 25. In this case, the four composite receiver coils 22a-d are each at the same distance from the composite excitation coil 21 and are also arranged at the same distance from one another. In this example, the four composite receiver coils 22a-d are arranged at a differential angle of 90 degrees with respect to one another in each case. A fifth directional sensitivity can be achieved by evaluating the signals from the composite receiver coils 22a and 22b or 22d and 22c. A sixth directional sensitivity can be achieved by evaluating the signals from the composite receiver coils 22b and 22c or 22a and 22d. The same scheme for generating further additional directional sensitivities can also be applied to the composite coil systems 30 and 40 mentioned below.

Figure 9:
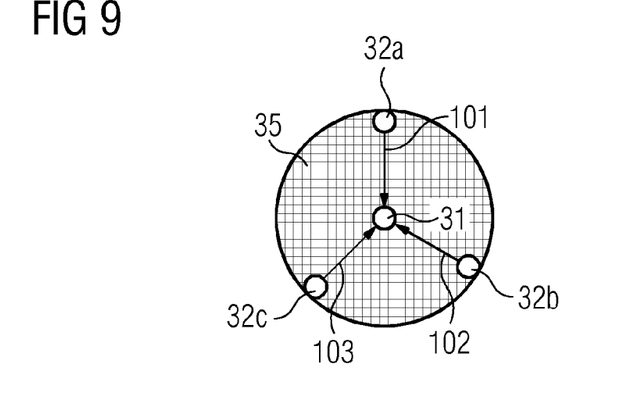
FIG. 9 schematically shows a second composite coil system as a fifth example of a sensor arrangement.

FIG. 9 shows such a second sensor arrangement which is provided by a second composite coil system 30. The latter comprises, as a first basic coil system, a composite excitation coil 31 and a first composite receiver coil 32a having a first direction 101 and a first directional sensitivity and, as a second basic coil system, comprises the composite excitation coil 31 and a second composite receiver coil 32b having a second direction 102 and a second directional sensitivity and, as a third basic coil system, comprises the composite excitation coil 31 and a third composite receiver coil 32c having a third direction 103 and a third directional sensitivity, the three composite receiver coils 32a, b, c being arranged on a common ferrite core 35. In this case, the three composite receiver coils 32a-c are at the same distance from the composite excitation coil 31 and are arranged at the same distance from one another. In this example, the three composite receiver coils 32a-c are arranged at a differential angle of 120 degrees with respect to one another.

Figure 10:
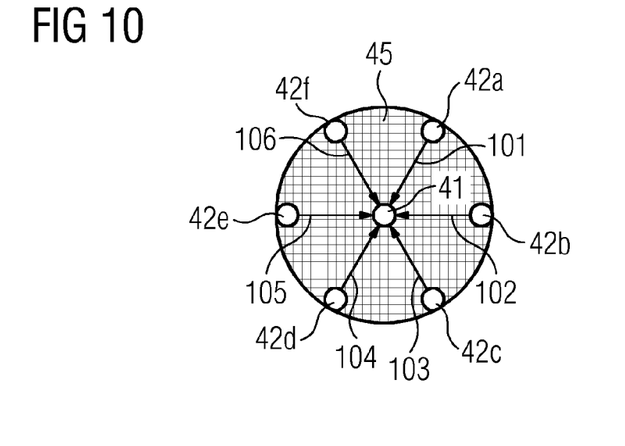
FIG. 10 schematically shows a third composite coil system as a sixth example of a sensor arrangement.

FIG. 10 shows such a third sensor arrangement which is provided by a third composite coil system 40. The latter comprises, as a first basic coil system, a composite excitation coil 41 and a first composite receiver coil 42a having a first direction 101 and a first directional sensitivity, as a second basic coil system, comprises the composite excitation coil 41 and a second composite receiver coil 42b having a second direction 102 and a second directional sensitivity and, as a third basic coil system, comprises the composite excitation coil 41 and a third composite receiver coil 42c having a third direction 103 and a third directional sensitivity. This sensor arrangement also comprises, as a further basic coil system, the composite excitation coil 41 and a fourth composite receiver coil 42d having a fourth direction 104 and a fourth directional sensitivity. This sensor arrangement also comprises, as a further basic coil system, the composite excitation coil 41 and a fifth composite receiver coil 42e having a fifth direction 105 and a fifth directional sensitivity. This sensor arrangement additionally comprises, as a further basic coil system, the composite excitation coil 41 and a sixth composite receiver coil 42f having a sixth direction 106 and a sixth directional sensitivity. In this case, the six composite receiver coils 42a-f and the composite excitation coil 41 are arranged on a common ferrite core 45. In this case, the six composite receiver coils 42a-f are at the same distance from the composite excitation coil 41 and are arranged at the same distance from one another. In this example, the six composite receiver coils 42a-f have a differential angle of 60 degrees with respect to one another.

It goes without saying that the number of composite receiver coils 22a-d, 32a-c, 42a-f is not restricted, nor is the number of composite excitation coils 21, 31, 41. As already mentioned above, in addition to a symmetrical arrangement, the arrangements having differential angles of 45 degrees, 60 degrees, 90 degrees (not shown) or 120 degrees also have the advantage of simple systems of equations, which is favorable for calculation.

Using more than three basic coil systems, such as in the composite coil systems, makes it possible to produce additional redundancies or to also carry out plausibility checks, for example.

The advantage of using a plurality of basic coil systems 1a-c lies in the simple producibility and availability of U, E, EI or other core forms, preferably ferrites, and the associated arrangement of the basic coil systems.

When electrically connecting these basic coil systems, it must be ensured that a sensitivity which is identical as possible can be achieved for all basic coil systems. In addition to the adjustment of the receiver coil, identical excitation should be ensured in this case, in particular. This can be advantageously ensured by means of an electrical series circuit of the excitation coils. The receiver coils in the examples illustrated should preferably be operated in a series circuit in one direction in the case of a plurality of basic coil systems (U basic coil system, EI basic coil system, composite coil systems). The angular orientations (or directions 101 to 106) which apply to the different directions of the basic coils should be inserted into the system of equations for Mohr's stress circle in order to calculate the stress tensor. Using more than three such basic coil systems makes it possible to produce additional redundancies or also to carry out plausibility checks, for example.

Checking workpieces 10 using the sensor arrangement according to embodiments of the invention makes it possible to draw conclusions on their microstructure changes in a non-destructive manner. In addition, the sensor arrangement according to embodiments of the invention, with the method according to embodiments of the invention, is suitable for permanently monitoring workpieces 10 in installations. It is therefore possible to detect, for example, fatigue of the material before damage becomes visible. Fractures or cracks can therefore be avoided. The sensor arrangement according to embodiments of the invention and the method according to embodiments of the invention operate contactlessly and in an application-free manner, that is to say the measurement can be carried out at any desired surface points of the workpiece 10 without apparatuses having to be fitted there.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

The invention claimed is:

1. A sensor arrangement for detecting at least one of the surface stresses and the microstructure state of a ferromagnetic workpiece, the sensor arrangement comprising:
a first basic coil system, a second basic coil system, and a third basic coil system, wherein each of the first basic coil system, second basic coil system, and third basic coil system comprise at least one excitation coil and at least one receiver coil;
wherein the first basic coil system has a first direction and a first directional sensitivity, the second basic coil system has a second direction and a second directional sensitivity, and the third basic coil system has a third direction and a third directional sensitivity;
the first basic coil system and the second basic coil system forming a first differential angle and the second basic coil system and the third basic coil system forming a second differential angle;
the first basic coil system being arranged outside the second directional sensitivity and the third directional sensitivity, the second basic coil system being arranged outside the first directional sensitivity and the third directional sensitivity, and the third basic coil system being arranged outside the first directional sensitivity and the second directional sensitivity, with the result that the mechanical surface stresses of the ferromagnetic workpiece can be at least partially determined using vector components based upon the directional sensitivity and direction of the first basic coil system, the second basic coil system and the third basic coil system and the first differential angle and second differential angle.

2. The sensor arrangement as claimed in claim 1, wherein the excitation coil and the receiver coil have a coil core with a coil core diameter, and the directional sensitivity is given by the ratio of the distance between the two coil cores and/or by the ratio of the two coil core diameters.

3. The sensor arrangement as claimed in claim 1, wherein at least one of the first basic coil system and the second basic coil system and the third basic coil system comprise(s) an excitation coil and a receiver coil which are arranged on a U ferrite core.

4. The sensor arrangement as claimed in claim 1, wherein at least one of the first basic coil system and the second basic coil system and the third basic coil system comprise(s) an excitation coil and a first receiver coil and a second receiver coil which are arranged on a U ferrite core, the excitation coil being arranged between, in particular centrally between, the first receiver coil and the second receiver coil.

5. The sensor arrangement as claimed in claim 1, wherein at least one of the first basic coil system and the second basic coil system and the third basic coil system comprise(s) an excitation coil and a first receiver coil and a second receiver coil which are arranged on an E ferrite core, the excitation coil being arranged, in particular centrally in the center, between the first receiver coil and the second receiver coil.

6. The sensor arrangement as claimed in claim 1 wherein at least two excitation coils of the first, second, and third basic coil systems have a series circuit.

7. The sensor arrangement of claim 1, further comprising a fourth basic coil system having an excitation coil and a receiver coil;
the fourth basic coil system having a fourth receiver coil;
wherein the first basic coil system, second basic coil system, third basic coil system, and fourth basic coil system all share a single excitation coil;
further wherein, the single excitation coil and the first, second, third, and fourth receiver coils are arranged on a common ferrite core.

8. The sensor arrangement as claimed in claim 7, wherein the four receiver coils are at the same distance from the single excitation coil, and adjacent receiver coils are each arranged at the same distance from one another.

9. The sensor arrangement of claim 1, wherein:
further wherein the first basic coil system, second basic coil system, and third basic coil system all share a single excitation coil;
further wherein the first, second, and third basic coil systems, including the shared single excitation coil, are arranged on a common ferrite core.

10. The sensor arrangement as claimed in claim 9, wherein the three receiver coils are at the same distance from the shared single excitation coil, and adjacent receiver coils are each arranged at the same distance from one another.

11. The sensor arrangement of claim 1, further comprising:
a fourth, fifth, and sixth basic coil system, each of the fourth, fifth, and sixth basic coil systems having an excitation coil and a receiver coil;
wherein the first basic coil system, second basic coil system, third basic coil system, fourth basic coil system, fifth basic coil system, and sixth basic coil system share a single excitation coil;
further wherein the first, second, third, fourth, fifth, and sixth basic coil systems, including the shared single excitation coil, are arranged on a common ferrite core.

12. The sensor arrangement as claimed in claim 11, wherein the six receiver coils are at the same distance from the shared single excitation coil, and adjacent receiver coils are each arranged at the same distance from one another.

13. The sensor arrangement as claimed in claim 1, wherein the first differential angle is equal to the second differential angle and is, in particular, 45 degrees.

14. The sensor arrangement as claimed in claim 1, wherein the first differential angle and the second differential angle are 60 degrees.

15. The sensor arrangement as claimed in claim 1, wherein the first differential angle and the second differential angle are 120 degrees.

16. The sensor arrangement as claimed in claim 1, wherein at least one coil axis is included, the sensor arrangement being arranged with respect to a surface of the workpiece in such a manner that an orthogonal orientation of the coil axis with respect to the surface of the workpiece is achieved, and the sensor arrangement being at a nominal distance from this surface of the ferromagnetic workpiece, at least the first basic coil system and the second basic coil system and the third basic coil system being at a distance of at most 20% of the nominal distance from one another.

17. The sensor arrangement as claimed in claim 1, wherein at least the first basic coil system and the second basic coil system and the third basic coil system are arranged on a suitable holding device.

18. A method for determining the mechanical surface stresses and/or the microstructure state of a ferromagnetic workpiece by means of the following steps:
determining at least three independent measured values by a sensor arrangement as claimed in claim 1, wherein the three independent measured values are provided by the first, second, and third basic coil systems;
determining the direction-dependent permeability at a particular measuring point by a computing algorithm.

19. The method as claimed in claim 18, wherein
a plurality of measuring points of the workpiece are determined and it is possible to determine a direction-dependent permeability therefrom, and the internal stress tensor is therefore mapped.

20. A sensor arrangement for detecting at least one of the surface stresses and the microstructure state of a ferromagnetic workpiece, the sensor arrangement comprising:
a composite excitation coil;
a first composite receiver coil;
a second composite receiver coil;
a third composite receiver coil;
a first composite coil system comprising the composite excitation coil and the first composite receiver coil;
a second composite coil system comprising the composite excitation coil and the second composite receiver coil;
a third composite coil system comprising the composite excitation coil and the third composite receiver coil;
wherein the first composite coil system has a first direction and a first directional sensitivity, the second composite coil system has a second direction and a second directional sensitivity, and the third composite coil system has a third direction and a third directional sensitivity;
the first composite coil system and the second composite coil system forming a first differential angle, the second composite coil system and the third composite coil system forming a second differential angle, and the third composite coil system and the first composite coil system forming a third differential angle;

wherein the mechanical surface stresses of the ferromagnetic workpiece can be at least partially determined using vector components based upon the directional sensitivity and direction of the first composite coil system, the second composite coil system, and the third composite coil system and the first differential angle, the second differential angle, and the third differential angle.

* * * * *